(12) United States Patent
Yamaguchi et al.

(10) Patent No.: US 8,796,309 B2
(45) Date of Patent: Aug. 5, 2014

(54) PHARMACEUTICAL COMPOSITION ACHIEVING EXCELLENT ABSORBENCY OF PHARMACOLOGICALLY ACTIVE SUBSTANCE

(75) Inventors: Yasuo Yamaguchi, Tokushima (JP); Takakuni Matsuda, Tokushima (JP); Yuso Tomohira, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1193 days.

(21) Appl. No.: 12/084,483

(22) PCT Filed: Nov. 2, 2006

(86) PCT No.: PCT/JP2006/321954
§ 371 (c)(1),
(2), (4) Date: Mar. 23, 2009

(87) PCT Pub. No.: WO2007/052738
PCT Pub. Date: May 10, 2007

(65) Prior Publication Data
US 2009/0227630 A1     Sep. 10, 2009

(30) Foreign Application Priority Data
Nov. 4, 2005    (JP) .................................. 2005-321191

(51) Int. Cl.
*A61K 31/445*        (2006.01)
(52) U.S. Cl.
USPC ......................................................... 514/322
(58) Field of Classification Search
USPC ................................ 514/183, 322
See application file for complete search history.

(56) References Cited

U.S. PATENT DOCUMENTS

2006/0094767 A1    5/2006    Tsubouchi et al.
2006/0134085 A1    6/2006    Yamaguchi

FOREIGN PATENT DOCUMENTS

| JP | 60-197618 | 10/1985 |
|---|---|---|
| JP | 7-39347 | 2/1995 |
| JP | 10-231254 | 9/1998 |
| JP | 2000-24487 | 1/2000 |
| JP | 2000-26283 | 1/2000 |
| JP | 2001-316259 | 11/2001 |
| JP | 2005-43 | 1/2005 |
| WO | WO 00/50007 | 8/2000 |
| WO | WO 01/12155 A1 | 2/2001 |
| WO | WO 2004/033463 A1 | 4/2004 |

OTHER PUBLICATIONS

English Language Translation of JP-10231254 (Feb. 1998), 24 pages.*
Masayuki et al, JP1998-231254, published Sep. 2, 1998, Machine Translation used for this Office Action.*

* cited by examiner

*Primary Examiner* — Jason Sims
*Assistant Examiner* — Ibrahim D Bori
(74) *Attorney, Agent, or Firm* — Finnegan, Henderson, Farabow, Garrett & Dunner, L.L.P.

(57) ABSTRACT

The present invention provides a pharmaceutical composition that can efficiently achieve its medicinal action by having excellent basic pharmacologically active substance absorbency, even the basic pharmacologically active substance is poorly soluble, the pharmaceutical composition being prepared by adding (i) a basic pharmacologically active substance together with (ii) a fatty acid and organic acid glycerol ester and/or fatty acid and organic acid polyglycerol ester.

10 Claims, 2 Drawing Sheets

PHARMACEUTICAL COMPOSITION ACHIEVING EXCELLENT ABSORBENCY OF PHARMACOLOGICALLY ACTIVE SUBSTANCE

FIELD OF THE INVENTION

The present invention relates to a pharmaceutical composition exhibiting excellent pharmacologically active substance absorbency in the alimentary canal, so that the medicinal action of a pharmacologically active substance contained therein can be efficiently achieved.

BACKGROUND OF THE INVENTION

The dissolution of a basic pharmacologically active substance increases under the acidic conditions of the alimentary canal, because a basic pharmacologically active substance is usually more soluble under acidic conditions. Therefore, the basic pharmacologically active substance is expected to exhibit the improved absorption in the alimentary canal. However, the absorbency of a basic pharmacologically active substance in the alimentary canal is difficult to improve merely by mixing the basic pharmacologically active substance with an acidic material, because the acidic material elutes, etc., soon after administration. Among basic pharmacologically active substances, particularly poorly soluble basic pharmacologically active substances often fail to achieve expected medicinal actions when taken orally, because they are not satisfactorily absorbed in the alimentary canal.

In order to enhance the absorbency of poorly soluble pharmacologically active substance in the alimentary canal, absorbefacients have often been used. However, absorbefacients have problems in terms of safety, because they may cause mucous membrane disorders, and/or enhance absorbency of components other than the target pharmacologically active substance.

The following methods have been reported for improving the absorbency of pharmacologically active substances. It has been reported that the absorbency of a pharmacologically active substance can be enhanced by combining a higher alcohol, a fatty acid or like oleophilic substance together with a pharmacologically active substance that is poorly soluble when orally taken (see Patent Document 1). It has also been reported that the absorbency of a pharmacologically active substance can be improved by using a hydrophobic pharmacologically active substance in combination with a hydrophilic surfactant and a hydrophobic surfactant (see Patent Document 2). Furthermore, it has also been reported that absorbency of a pharmacologically active substance can be improved by using a hydrophilic pharmacologically active substance together with at least two surfactants (see Patent Document 3). However, merely by using a pharmacologically active substance together with an oleophilic substance or using specific surfactants in combination, satisfactory absorbency of pharmacologically active substance cannot be attained, and therefore it is difficult to satisfactorily absorb a poorly soluble pharmacologically active substance in the alimentary canal.

In light of such problems of the prior art techniques, development of a pharmaceutical composition having excellent basic pharmacologically active substance absorbency, and in particular, a pharmaceutical composition of which poorly soluble basic pharmacologically active component can be satisfactorily absorbed in the alimentary canal so that its medicinal action can be efficiently achieved in vivo, has been awaited.

[Patent Document 1] Japanese Unexamined Patent Publication No. 1998-231254
[Patent Document 2] WO00/50007
[Patent Document 3] WO01/012155

DISCLOSURE OF THE INVENTION

Problem to be Solved by the Invention

An object of the present invention is to solve the above-mentioned problems of the prior art techniques. More specifically, an object of the present invention is to provide a pharmaceutical composition imparting an improved absorbency of a basic pharmacologically active substance, so that its medicinal activity can be efficiently achieved even when the pharmacologically active substance contained is a poorly soluble basic pharmacologically active substance.

Means for Solving the Problem

The present inventors conducted extensive research to solve the above problems and found that absorbency of a basic pharmacologically active substance in the alimentary canal can be enhanced by using (i) a basic pharmacologically active substance together with (ii) a fatty acid and organic acid glycerol ester and/or a fatty acid and organic acid polyglycerol ester, and that even if the basic pharmacologically active substance is poorly soluble, its medicinal action can be efficiently achieved in vivo. The present invention was accomplished based on this finding.

In other words, the present invention provides pharmaceutical compositions as below:

Item 1. A pharmaceutical composition containing Component (i) a basic pharmacologically active substance, and Component (ii) a fatty acid and organic acid glycerol ester and/or a fatty acid and organic acid polyglycerol ester.

Item 2. (i) A pharmaceutical composition according to Item 1, wherein the basic pharmacologically active substance of Component (i) is a poorly soluble basic pharmacologically active substance.

Item 3. A pharmaceutical composition according to Item 1, wherein the basic pharmacologically active substance of Component (i) is a 2,3-dihydroimidazo[2,1-b]oxazole compound represented by General Formula (1)

[Chemical Formula 1]

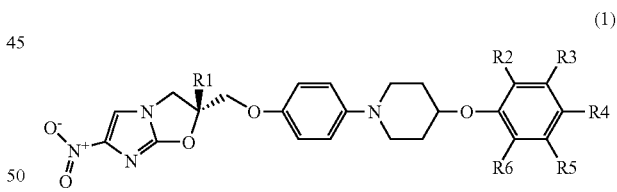

(1)

wherein $R_1$ is a hydrogen atom or a $C_1$-$C_6$ alkyl group; and $R_2$-$R_6$ are independently a hydrogen atom, or a halogen substituted or unsubstituted $C_1$-$C_6$ alkyl group.

Item 4. A pharmaceutical composition according to Item 1, wherein the basic pharmacologically active substance of Component (i) is caffeine.

Item 5. A pharmaceutical composition according to Item 1, wherein the constituent organic acid of Component (ii), a fatty acid and organic acid glycerol ester and/or a fatty acid and organic acid polyglycerol ester, is at least one member selected from the group consisting of citric acid, acetic acid, lactic acid, succinic acid, tartaric acid, diacetyltartaric acid, malic acid, ascorbic acid, and fumaric acid.

Item 6. A pharmaceutical composition according to Item 1, wherein the constituent organic acid of Component (ii), a fatty acid and organic acid glycerol ester and/or a fatty acid and organic acid polyglycerol ester, is a divalent or higher valencent organic acid having carboxyl group(s).

Item 7. A pharmaceutical composition according to Item 1, wherein the constituent fatty acid of Component (ii), a fatty acid and organic acid glycerol ester and/or a fatty acid and organic acid polyglycerol ester, is a saturated or unsaturated $C_6$-$C_{24}$ fatty acid.

Item 8. A pharmaceutical composition according to Item 1, wherein Component (ii) is at least one member selected from the group consisting of citric acid and fatty acid glycerol esters, acetic acid and fatty acid glycerol esters, lactic acid and fatty acid glycerol esters, succinic acid and fatty acid glycerol esters, fumaric acid and fatty acid glycerol esters, tartaric acid and fatty acid glycerol esters, diacetyltartric acid and fatty acid glycerol esters, citric acid and fatty acid polyglycerol esters, acetic acid and fatty acid polyglycerol esters, lactic acid and fatty acid polyglycerol esters, succinic acid and fatty acid polyglycerol esters, fumaric acid and fatty acid polyglycerol esters, tartaric acid and fatty acid polyglycerol esters, and diacetyltartric acid and fatty acid polyglycerol esters.

Item 9. A pharmaceutical composition according to Item 1, wherein Component (ii) is a fatty acid and organic acid glycerol ester, wherein the constituent organic acid is citric acid and the constituent fatty acid is at least one member selected from the group consisting of caprylic acid, stearic acid, oleic acid, and behenic acid.

Item 10. A pharmaceutical composition according to Item 1, which contains 10 to 100000 parts by weight of Component (ii) per 100 parts by weight of Component (i).

Item 11. A pharmaceutical composition according to Item 1, which contains 0.1 to 80 wt. % of Component (i) and 1 to 99.5 wt. % of Component (ii) per total weight of the pharmaceutical composition.

Item 12. A pharmaceutical composition according to Item 1, which further contains at least one member selected from the group consisting of oil-based materials, hydrophilic surfactants, and oleophilic surfactants.

The present invention further provides methods for preparing pharmaceutical compositions as follows:

Item 13. A method for preparing a basic pharmacologically active substance-containing pharmaceutical composition comprising a step of combining:
(i) a basic pharmacologically active substance; with
(ii) a fatty acid and organic acid glycerol ester and/or a fatty acid and organic acid polyglycerol ester.

Item 14. A method according to Item 13, wherein the basic pharmacologically active substance of Component (i) is a poorly soluble pharmacologically active substance.

Item 15. A method according to Item 13, wherein the basic pharmacologically active substance of Component (i) is a 2,3-dihydroimidazo[2,1-b]oxazole compound represented by General Formula (1):

[Chemical Formula 2]

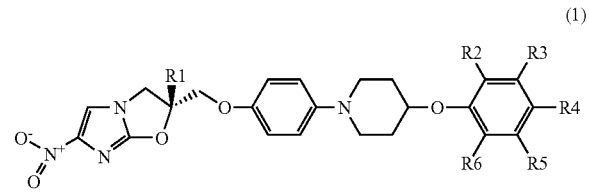

(1)

wherein $R_1$-$R_6$ are the same as in Item 3.

Item 16. A method according to Item 13, wherein the basic pharmacologically active substance of Component (i) is caffeine.

Item 17. A method according to Item 13, wherein the constituent organic acid of Component (ii), a fatty acid and organic acid glycerol ester and/or a fatty acid and organic acid polyglycerol ester, is at least one member selected from the group consisting of citric acid, acetic acid, lactic acid, succinic acid, tartaric acid, diacetyltartaric acid, malic acid, ascorbic acid, and fumaric acid.

Item 18. A method according to Item 13, wherein the constituent organic acid of Component (ii), a fatty acid and organic acid glycerol ester and/or a fatty acid and organic acid polyglycerol ester, is a divalent or higher valent organic acid having carboxyl group(s).

Item 19. A method according to Item 13, wherein the constituent fatty acid of Component (ii), a fatty acid and organic acid glycerol ester and/or a fatty acid and organic acid polyglycerol ester, is a saturated or unsaturated $C_6$-$C_{24}$ fatty acid.

Item 20. A method according to Item 13, wherein Component (ii) is at least one member selected from the group consisting of citric acid and fatty acid glycerol esters, acetic acid and fatty acid glycerol esters, lactic acid and fatty acid glycerol esters, succinic acid and fatty acid glycerol esters, fumaric acid and fatty acid glycerol esters, tartaric acid and fatty acid glycerol esters, diacetyltartric acid and fatty acid glycerol esters, citric acid and fatty acid polyglycerol esters, acetic acid and fatty acid polyglycerol esters, lactic acid and fatty acid polyglycerol esters, succinic acid and fatty acid polyglycerol esters, fumaric acid and fatty acid polyglycerol esters, tartaric acid and fatty acid polyglycerol esters, and diacetyltartric acid and fatty acid polyglycerol esters.

Item 21. A method according to Item 13, wherein Component (ii) is a fatty acid and organic acid glycerol ester, wherein the constituent organic acid is citric acid and the constituent fatty acid is at least one member selected from the group consisting of caprylic acid, stearic acid, oleic acid, and behenic acid.

Item 22. A method according to Item 13, which comprises the step of adding 10 to 100000 parts by weight of Component (ii) per 100 parts by weight of Component (i).

Item 23. A method according to Item 13, which comprises the step of adding 0.1 to 80 wt. % of Component (i) and 1 to 99.5 wt. % of Component (ii) per total weight of the pharmaceutical composition.

Item 24. A method according to Item 13, which comprises the step of further adding at least one member selected from the group consisting of oil-based materials, hydrophilic surfactants, and oleophilic surfactants.

The present invention provides the following uses:

Item 25. Use of Component (ii), a fatty acid and organic acid glycerol ester and/or a fatty acid and organic acid polyglycerol ester, for the production of a pharmaceutical composition comprising (i) a basic pharmacologically active substance.

Item 26. Use according to Item 25, wherein the basic pharmacologically active substance of Component (i) is a poorly soluble basic pharmacologically active substance.

Item 27. Use according to Item 25, wherein the basic pharmacologically active substance of Component (i) is a 2,3- dihydroimidazo[2,1-b]oxazole compound represented by General Formula (1):

[Chemical Formula 3]

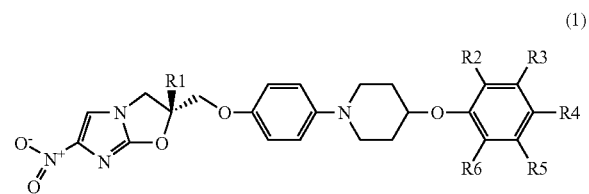

(1)

wherein $R_1$-$R_6$ are the same as in Item 3.

Item 28. Use according to Item 25, wherein the basic pharmacologically active substance of Component (i) is caffeine.

Item 29. Use according to Item 25, wherein the constituent organic acid of Component (ii), a fatty acid and organic acid glycerol ester and/or a fatty acid and organic acid polyglycerol ester, is at least one member selected from the group consisting of citric acid, acetic acid, lactic acid, succinic acid, tartaric acid, diacetyltartaric acid, malic acid, ascorbic acid, and fumaric acid.

Item 30. Use according to Item 25, wherein the constituent organic acid of Component (ii), a fatty acid and organic acid glycerol ester and/or a fatty acid and organic acid polyglycerol ester, is a divalent or higher valent organic acid having carboxyl group(s).

Item 31. Use according to Item 25, wherein the constituent fatty acid of Component (ii), a fatty acid and organic acid glycerol ester and/or a fatty acid and organic acid polyglycerol ester, is a saturated or unsaturated $C_6$-$C_{24}$ fatty acid.

Item 32. Use according to Item 25, wherein Component (ii) is at least one member selected from the group consisting of citric acid and fatty acid glycerol esters, acetic acid and fatty acid glycerol esters, lactic acid and fatty acid glycerol esters, succinic acid and fatty acid glycerol esters, fumaric acid and fatty acid glycerol esters, tartaric acid and fatty acid glycerol esters, diacetyltartric acid and fatty acid glycerol esters, citric acid and fatty acid polyglycerol esters, acetic acid and fatty acid polyglycerol esters, lactic acid and fatty acid polyglycerol esters, succinic acid and fatty acid polyglycerol esters, fumaric acid and fatty acid polyglycerol esters, tartaric acid and fatty acid polyglycerol esters, and diacetyltartric acid and fatty acid polyglycerol esters.

Item 33. Use according to Item 25, wherein Component (ii) is a fatty acid and organic acid glycerol ester, wherein the constituent organic acid is citric acid and the constituent fatty acid is at least one member selected from the group consisting of caprylic acid, stearic acid, oleic acid, and behenic acid.

Item 34. Use according to Item 25, wherein 10 to 100000 parts by weight of Component (ii) is added per 100 parts by weight of Component (i).

Item 35. Use according to Item 25, wherein 0.1 to 80 wt. % of Component (i) and 1 to 99.5 wt. % of Component (ii) are added per total weight of the pharmaceutical composition.

Item 36. Use according to Item 25, wherein the pharmaceutical composition further comprises at least one member selected from the group consisting of oil-based materials, hydrophilic surfactants, and oleophilic surfactants.

Effect of the Invention

Figure 1:
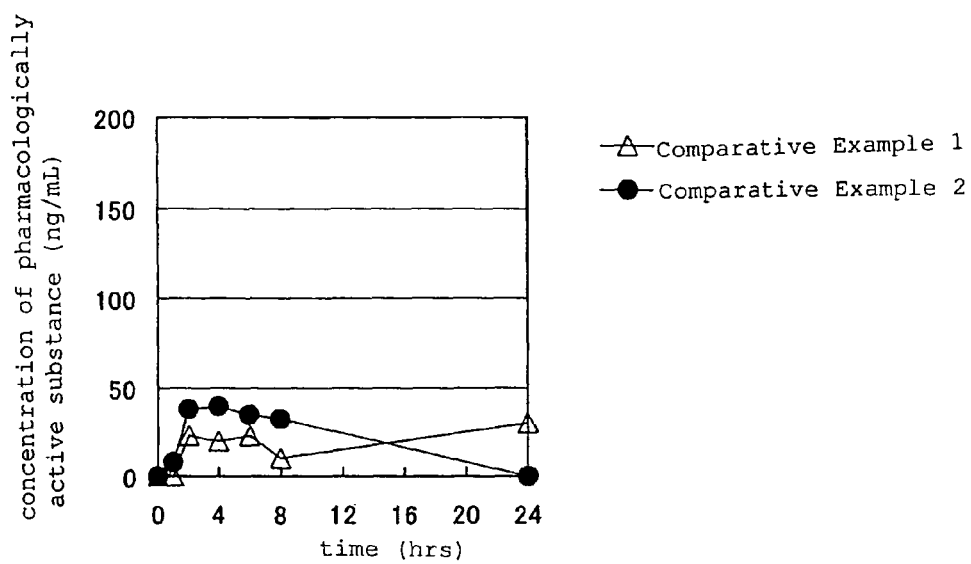
FIG. 1 shows the change over time of the average concentration of pharmacologically active substance (2,3-dihydroimidazo[2,1-b]oxazole compound (1a)) in the blood in Comparative Test Example 1, when the pharmaceutical composition of Comparative Example 1 or 2 was orally administered to beagles.

The pharmaceutical composition of the present invention can effectively achieve its medicinal action in vivo because the orally taken pharmacologically active substance is efficiently absorbed in the alimentary by using Component (ii), i.e., a fatty acid and organic acid glycerol ester and/or a fatty acid and organic acid polyglycerol ester, together with the pharmacologically active substance. In prior art techniques, when a poorly soluble basic pharmacologically active substance is orally taken, because of its poor absorbency, expected medicinal actions cannot be satisfactorily attained; however, the pharmaceutical active ingredient of the present invention can effectively achieve medicinal actions in vivo because its pharmaceutical composition can be satisfactorily absorbed in the alimentary canal even if it is a poorly soluble basic pharmacologically active substance.

BEST MODE FOR CARRYING OUT THE INVENTION

The present invention is explained in detail below.

The pharmacologically active substance contained in the pharmaceutical composition of the present invention is (i) a basic pharmacologically active substance (and may be referred to as Component (i)). The basic pharmacologically active substance contains one or more moieties selected from the group consisting of amino groups, amidino groups, guanidino groups, ammonium groups, cyclic amino groups, nucleic acid base and like basic groups. There are no restrictions on the number and positions of such basic groups in the basic pharmacologically active substance. There are no limitations on the types and medicinal actions of the basic pharmacologically active substances usable in the present invention as long as they can taken orally. Examples of basic pharmacologically active substances usable in the present invention include antitubercular agents, antitumor agents, chemotherapy agents, platelet aggregation prevention agents, anti-allergic agents, antihistamines, cardiotonic agents, antiarrhythmic agents, diuretics, hypnotic sedative agents, antiepileptic agents, antidepressants, local anesthetics, muscle relaxants, antihypertensive agents, vasoconstriction agents, vasodilator agents, antitussive agents, expectorants, medicines for intestinal disorders, antipeptic ulcer agents, purgatives, cold medicines, agents affecting respiratory organs, agents affecting digestive organs, agents affecting circulatory organs, agents affecting central nervous systems, agents affecting peripheral nerves, antibiotics, pain-relievers, anti-inflammatory agents, antimicrobial agents, antidiabetic agents, antivirus agents, nutritional supplements, immunosuppressive agents, medicines for urinary incontinence, antiemetic agents, etc.

Specific examples of such basic pharmacologically active substances include diphenhydramine hydrochloride, methylephedrine hydrochloride, maprotiline hydrochloride, papaverine hydrochloride, meclofenoxate hydrochloride, phenylephrine hydrochloride, ephedrine hydrochloride, norepinephrine, berberine chloride, cetraxate hydrochloride, sulfamethoxazole, metronidazole, diazepam, cimetidine, famotidine, cloperastine hydrochloride, noscapine hydrochloride, bloghexine hydrochloride, diphenidol hydrochloride, promethazine hydrochloride, alimemazine tartrate, caffeine, digoxin, procainamide hydrochloride, propranolol hydrochloride, hydralazine hydrochloride, verapamil hydrochloride, cefotiam hexetil hydrochloride, erythromycin, clarithromycin, kitasamycin, josamycin, roxithromycin, midecamycin, etc.

The pharmaceutical composition of the present invention can effectively achieve medicinal action by enhancing absorbency even if the pharmacologically active substance is a poorly soluble substance, which is barely soluble in water and exhibiting very low absorbency. In light of the effects of the invention, a preferable example of Component (i) in the pharmaceutical composition of the present invention is a poorly soluble basic pharmacologically active substance. Here, the poorly soluble basic pharmacologically active substance corresponds to a drug whose solubility is in the categories of "sparingly soluble", "slightly soluble", "very slightly soluble" or "partially insoluble or insoluble" defined in the general notice of the Japanese Pharmacopoeia. In the general notice of the Japanese Pharmacopoeia, solubility of a pharmacologically active substance is determined by solubility of the pharmacologically active substance, previously powdered in the case of a solid, within 30 minutes of being placed in a solvent at 20±5° C., with vigorously shaking for 30 seconds each time at 5-minutes interval. Specifically, "sparingly soluble" indicates a condition wherein not less than 30 mL but not more than 100 mL water is necessary to dissolve 1 g or 1 mL of pharmacologically active substance; "slightly soluble" indicates a condition wherein not less than 100 mL but not more than 1000 mL water is necessary to dissolve 1 g or 1 mL of pharmacologically active substance; "very slightly soluble" indicates a condition wherein not less than 1000 mL but not more than 10000 mL water is necessary to dissolve 1 g or 1 mL of pharmacologically active substance; and "partially insoluble or insoluble" indicates a condition wherein more than 10000 mL water is necessary to dissolve 1 g or 1 mL of pharmacologically active substance.

Specific examples of such poorly soluble basic pharmacologically active substances include maprotiline hydrochloride, papaverine hydrochloride, norepinephrine, berberine chloride, cetraxate hydrochloride, sulfamethoxazole, metronidazole, diazepam, cimetidine, famotidine, bloghexine hydrochloride, diphenidol hydrochloride, caffeine, digoxin, verapamil hydrochloride, erythromycin, clarithromycin, kitasamycin, josamycin, roxithromycin, midecamycin, etc.

As well as the above-exemplified basic pharmacologically active substances, a 2,3-dihydroimidazo[2,1-b]oxazole compound represented by General Formula (1) is also a preferably usable example in the pharmaceutical composition of the present invention. Such a compound is poorly soluble but exhibits excellent antimicrobial activity against tubercle bacilli, drug-resistant tubercule bacilli and atypical mycobacteria, and therefore it is a pharmacologically usable compound. The pharmaceutical composition of the present invention effectively increases absorbency of a 2,3-dihydroimidazo[2,1-b]oxazole compound in the alimentary canal, and therefore the pharmaceutical composition of the present invention is preferably used for preparing a 2,3-dihydroimidazo[2,1-b]oxazole compound into pharmaceutical preparations.

[Chemical Formula 4]

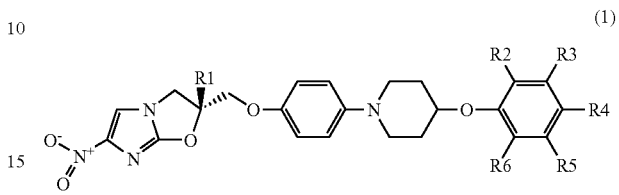

(1)

In General Formula (1), R1 is a hydrogen atom or a $C_1$-$C_6$ alkyl group, and preferably a methyl group or an ethyl group.

R2-R6 are independently a hydrogen atom, halogen substituted or unsubstituted $C_1$-$C_6$ alkyl group, or halogen substituted or unsubstituted $C_1$-$C_6$ alkoxy group, and preferably a hydrogen atom, halogen substituted or unsubstituted $C_1$-$C_3$ alkyl group, or halogen substituted or unsubstituted $C_1$-$C_3$ alkoxy group. In particular, it is preferable that R2, R3, R5 and R6 be hydrogen atoms and $R_4$ be a halogen substituted or unsubstituted $C_1$-$C_3$ alkoxy group.

One example of a preferable 2,3-dihydroimidazo[2,1-b]oxazole compound represented by General Formula (1) is the 2,3-dihydroimidazo[2,1-b]oxazole compound (1a) shown below, wherein R1 is a methyl group; R2, R3, R5 and R6 are hydrogen atoms; and R4 is a trifluoromethoxy group.

[Chemical Formula 5]

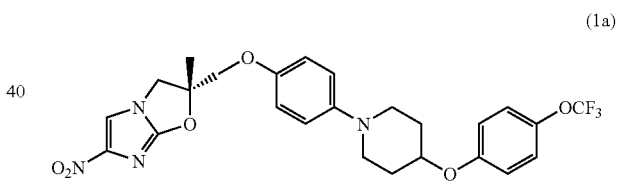

(1a)

Note that the definition of the groups represented by R1-R6 in General Formula (1) is as follows.

A $C_1$-$C_6$ alkyl group is a straight or branched-chain alkyl group having 1 to 6 carbon atoms, such as a methyl, ethyl, n-propyl, isopropyl, n-butyl, isobutyl, tert-butyl, sec-butyl, n-pentyl, neopentyl, n-hexyl, isohexyl, and 3-methylpentyl groups, etc.

A halogen substituted or unsubstituted $C_1$-$C_6$ alkyl group is an above-defined straight or branched-chain alkyl group having 1 to 6 carbon atoms or such an alkyl group with 1 to 7 halogen substituents. Specific examples thereof include methyl, ethyl, n-propyl, isopropyl, n-butyl, isobutyl, tert-butyl, sec-butyl, n-pentyl, neopentyl, n-hexyl, isohexyl, 3-methylpentyl, fluoromethyl, difluoromethyl, trifluoromethyl, chloromethyl, dichloromethyl, trichloromethyl, bromomethyl, dibromomethyl, dichlorofluoromethyl, 2,2,2-trifluoroethyl, pentafluoroethyl, 2-chloroethyl, 3,3,3-trifluoropropyl, heptafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, and 6-chlorohexyl groups, etc.

A halogen substituted or unsubstituted $C_1$-$C_6$ alkoxy group is a $C_1$-$C_6$ alkoxy group formed of an above-defined $C_1$-$C_6$ alkyl group and an oxygen atom, or such an alkoxy group with 1 to 7 halogen substitutents. Specific examples thereof include methoxy, ethoxy, n-propoxy, isopropoxy, n-butoxy, isobutoxy, tert-butoxy, sec-butoxy, n-pentoxy, neopentoxy, n-hexyloxy, isohexyloxy, 3-methylpentoxy, fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentoxy, 5-chloropentoxy, 6,6,6-trifluorohexyloxy, and 6-chlorohexyloxy groups, etc.

2,3-dihydroimidazo[2,1-b]oxazole compounds represented by General Formula (1) are known compounds disclosed by Japanese Unexamined Patent Publication No. 2004-149527, and can be synthesized according to the method disclosed in that document.

The dose of Component (i) of the pharmaceutical composition of the present invention per day depends on the type of Component (i), and gender, age and the like of the patient, but the dose is generally selected so that Component (i) is taken in an amount of about 0.1 to 2000 mg, and preferably about 0.5 to 1000 mg, per day per adult.

The content of Component (i) in the pharmaceutical composition of the present invention may be suitably selected depending on the gender, age and the like of the patient; administration route; form of preparation; type and dose of Component (i), etc. The content of Component (i) is generally 0.1 to 80 wt. %, preferably 0.5 to 70 wt. %, and more preferably 1 to 60 wt. % per total weight of the pharmaceutical composition.

The pharmaceutical composition of the present invention contains (ii) a fatty acid and organic acid glycerol ester and/or a fatty acid and organic acid polyglycerol ester (and may be referred to as "Component (ii)") to improve absorbency of Component (i).

A fatty acid and organic acid glycerol ester (fatty acid and organic acid monoglycerol ester) is a compound wherein one or two fatty acids and one or two organic acids are linked to a glycerol by ester linkages.

Examples of constituent organic acids in the fatty acid and organic acid glycerol ester include citric acid, acetic acid, lactic acid, succinic acid, tartaric acid, diacetyltartaric acid, malic acid, ascorbic acid, fumaric acid, etc. In terms of improvement in absorbency of Component (i), preferable constituent organic acids are organic acids having a carboxyl group of divalence or higher valence (specifically, citric acid, succinic acid, tartaric acid, diacetyltartaric acid, malic acid, fumaric acid, etc.). Preferable examples of constituent organic acids of the fatty acid and organic acid glycerol ester include citric acid, succinic acid, tartaric acid, diacetyltartaric acid, and fumaric acid. Among these, citric acid is particularly preferable.

Examples of constituent fatty acids of the fatty acid and organic acid glycerol ester include a saturated or unsaturated $C_6$-$C_{24}$ fatty acid. Preferable examples of the constituent fatty acids include $C_8$-$C_{22}$ fatty acids, specifically caproic acid, caprylic acid, capric acid, lauric acid, myristic acid, palmitic acid, stearic acid, oleic acid, linoleic acid, linolenic acid, arachidonic acid, behenic acid, etc.

Specific examples of fatty acid and organic acid glycerol esters usable in the present invention include citric acid and fatty acid glycerol esters, succinic acid and fatty acid glycerol esters, acetic acid and fatty acid glycerol esters, lactic acid and fatty acid glycerol esters, diacetyltartaric acid and fatty acid glycerol esters, etc. In order to obtain extremely excellent absorbency Component (i), use of citric acid and fatty acid glycerol esters, succinic acid and fatty acid glycerol esters, tartaric acid and fatty acid glycerol esters, diacetyltartaric acid and fatty acid glycerol esters, and/or fumaric acid and fatty acid glycerol esters is preferable, and use of citric acid and fatty acid glycerol esters is particularly preferable.

A fatty acid and organic acid polyglycerol ester is a compound having one or more fatty acids and one or more organic acids bonded to a polyglycerol by ester linkages. In the fatty acid and organic acid polyglycerol ester, the upper limit of the total number of the bonded fatty acids and organic acids is, in the case of a straight or branched-chain polyglycerol, the number of polymerized constituent polyglycerols plus 2, and in the case of a cyclic polyglycerol, the number of polymerized constituent polyglycerols. There is no particular limitation on the degree of polymerization of the fatty acid and organic acid polyglycerol ester as long as a suitable number not exceeding the upper limit of fatty acids and organic acids are bonded. There is no limitation on the degree of polymerization of the constituent polyglycerol of the fatty acid and organic acid polyglycerol ester, but a suitable example is an average degree of polymerization of typically 2 to 15, and preferably 2 to 10. The same definitions can be applied to organic acids and fatty acids forming a fatty acid and organic acid polyglycerol ester, as those forming a fatty acid and organic acid glycerol ester.

Specific examples of fatty acid and organic acid polyglycerol esters usable in the present invention include citric acid and fatty acid polyglycerol esters, succinic acid and fatty acid polyglycerol esters, acetic acid and fatty acid polyglycerol esters, lactic acid and fatty acid polyglycerol esters, tartaric acid and fatty acid polyglycerol esters, diacetyltartric acid and fatty acid polyglycerol esters, fumaric acid and fatty acid polyglycerol esters, etc. Among these, citric acid and fatty acid polyglycerol esters, succinic acid and fatty acid polyglycerol esters, tartaric acid and fatty acid polyglycerol esters, diacetyltartric acid and fatty acid polyglycerol esters, and fumaric acid and fatty acid polyglycerol esters are preferable, and citric acid and fatty acid polyglycerol esters are particularly preferable.

Fatty acid and organic acid glycerol esters and fatty acid and organic acid polyglycerol esters are known compounds and can be prepared by known methods.

A preferable example of Component (ii) of the pharmaceutical composition of the present invention is a fatty acid and organic acid glycerol ester, and more preferable example thereof is a fatty acid and organic acid glycerol ester, wherein the constituent organic acid is citric acid and the constituent fatty acid is at least one member selected from the group consisting of caprylic acid, stearic acid, oleic acid, and behenic acid.

In the pharmaceutical composition of the present invention, there are no limitations on the proportion of Component (i) to Component (ii), but generally 10 to 100000 parts by weight, preferably 20 to 70000 parts by weight, and particularly preferably 30 to 50000 parts by weight of Component (ii) is contained per 100 parts by weight of Component (i). With such a proportion, the absorbency of Component (i) when orally taken can be significantly improved.

The content of Component (ii) in the pharmaceutical composition of the present invention may be suitably selected depending on the proportion of Component (i) to Component (ii), and the content of Component (i). For example, the content of Component (ii) is generally 1 to 99.5 wt. %, preferably 2 to 99 wt. %, and more preferably 5 to 90 wt. % of total weight of the pharmaceutical composition.

The pharmaceutical composition of the present invention may contain oil-based materials in addition to Component (i) and Component (ii). There are no limitations on such oil-based materials as long as they are pharmaceutically acceptable, and examples thereof include soybean oil, purified soybean oil, soya bean hardened oil, soybean oil unsaponifiable matters, squalene, castor oil, clove oil, trioleic acid sorbitan, turpentine oil, safflower oil, safflower oil fatty acid, oleic acid, coconut oil, rape seed oil, fusel oil, olive oil, linseed oil, sesame oil, chlorophyll oil, croton seed oil, bergamot oil, cedar oil, orange oil, fennel oil, eucalyptus oil, corn oil, lavender oil, sweet marjoram oil, lemon oil, cotton seed oil, egg yolk oil, rose oil, pineapple oil, almond oil, peanut oil, camellia oil, camphor white oil, German chamomile oil, cinnamon oil, mint oil, esterified corn oil, ginger oil, roman chamomile oil, snake oil, spearmint oil, sunflower seed oil, cacao butter, wheat germ oil, zinc oxide oils, hardened oils, hydrogenated vegetable oils, light liquid paraffin, liquid paraffin, triglycerides, diglycerides, mink oil, bitter orange peel oil, processed oils, etc. These oil-based materials may be used singly or in combination. Among these, triglycerides and diglycerides are suitably used in the present invention. Both medium chain fatty acid triglycerides and long chain fatty acid triglycerides can be used as triglycerides. Both medium chain fatty acid diglycerides and long chain fatty acid diglycerides can be used as diglycerides. Oils and fats containing triglycerides and/or diglycerides (e.g., vegetable oils, fish oils, animal fats, hardened vegetable oils, partially hardened vegetable oils, etc.) may be used as triglycerides and diglycerides. Suitable examples of medium chain fatty acids include $C_6$-$C_{13}$ fatty acids, and suitable examples of long chain fatty acids include $C_{14}$-$C_{22}$ fatty acids.

The content of oil-based materials is not limited, but, for example, the oil-based material content is generally 0.1 to 99.5 wt. %, preferably 0.5 to 97 wt. %, and more preferably 5 to 90 wt. % per total weight of the pharmaceutical composition.

The pharmaceutical composition of the present invention may additionally contain hydrophilic surfactants, oleophilic surfactants and/or like surfactants. By containing such surfactant(s), dispersibility and wettability of pharmacologically active substance can be improved and the viscosity of the composition can be controlled. Specific examples of such surfactants include Polysorbate 80, Polysorbate 20, propylene glycol fatty acid esters, glycerol/propylene glycol fatty acid esters, glycerol fatty acid esters, polyoxyethylene glycerol fatty acid esters, polyglycerol fatty acid esters, sorbitan fatty acid esters, polyoxyethylene sorbitan fatty acid esters, polyoxyethylene sorbitol fatty acid esters, polyoxyethylene castor oil/hardened castor oil, polyoxyethylene sterol/hydrogenated sterol, polyethylene glycol fatty acid esters, polyethylene glycol glycerol fatty acid esters, polyoxyethylene alkyl ethers, polyoxyethylene polyoxypropylene alkyl ethers, polyoxyethylene glycol alkyl ethers, polyethylene glycolsorbitan fatty acid esters, cholesterol and cholesterol derivatives, sugar esters, lower alcohol fatty acid esters, fatty acid salts, bile salts, phosphatide, etc. Among these, Polysorbate 80, glycerol fatty acid esters, propylene glycol fatty acid esters, polyoxyethylene glycerol fatty acid esters, and polyethylene glycol fatty acid esters are preferably usable in the present invention.

The pharmaceutical composition of the present invention may further contain, if necessary, excipients, disintegrators, diluting agents, preservatives, stabilizers, dispersants, gelling agents, suspending agents, emulsifiers, antiseptics, solubilizing agents, resolvents and like additives. The contents of these additives may be suitably selected depending on the use of the pharmaceutical composition and form of the composition.

There are no limitations on the forms of the pharmaceutical composition of the present invention as long as it can be orally taken, and examples thereof include tablets, granules, powders, solutions, suspensions, emulsions, gels, etc. It is also possible to form the pharmaceutical composition of the present invention into capsules by being placed in microcapsules, soft capsules, hard capsules, etc.

The pharmaceutical composition of the present invention can be prepared by a known method. For example, the pharmaceutical composition of the present invention can be prepared by mixing suitable amounts of Component (i), Component (ii), and optionally other components, and preparing the mixture into a suitable preparation form.

The absorbency of Component (i) in the alimentary canal can be improved by adding Component (ii). Therefore, the present invention also provides the use of Component (ii) for the production of a Component (i) containing pharmaceutical composition which is improved absorbency of Component (i) in the alimentary canal.

EXAMPLES

The present invention is explained in detail below based on Examples and Test Examples; however, the present invention is not limited to these.

Example 1

To a mixture solution of 400 mg of citric acid and oleic acid monoglycerol ester (Poem K-37 V: product of Riken Vitamin Co., Ltd.) and 200 mg of medium chain (mainly $C_6$-$C_{12}$) fatty acid triglycerides (ODO-H: product of Nisshin OilliO Group, Ltd.) was added 100 mg of 2,3-dihydroimidazo[2,1-b]oxazole compound (1a), giving a uniformly dispersed and suspended pharmaceutical composition.

Example 2

To a mixture solution of 400 mg of fatty acid and organic acid glycerol ester (Glyceryl citrate/lactate/linoleate/oleate, Imwitor 375: procured from Mitsuba Trading Co., Ltd.) [mixture wherein 1 to 3 organic acids (citric acid and/or lactic acid) and 1 to 3 fatty acids (linoleic acid and/or oleic acid) are bonded to monoglycerol and diglycerol] and 200 mg of medium chain fatty acid triglycerides (ODO-H: product of Nisshin OilliO Group, Ltd.) was added 100 mg of 2,3-dihydroimidazo[2,1-b]oxazole compound (1a), giving a uniformly dispersed and suspended pharmaceutical composition.

Example 3

To a mixture solution of 400 mg of citric acid and oleic acid monoglycerol ester (Poem K-37 V: product of Riken Vitamin Co., Ltd.) and 200 mg of a propylene glycol fatty acid ester (Miglyol 840: procured from Mitsuba Trading Co., Ltd.) was added 100 mg of 2,3-dihydroimidazo[2,1-b]oxazole compound (1a), giving a uniformly dispersed and suspended pharmaceutical composition.

Example 4

To a mixture solution of 400 mg of citric acid and oleic acid monoglycerol ester (Poem K-37 V: product of Riken Vitamin Co., Ltd.), 100 mg of a propylene glycol fatty acid ester (Miglyol 840: procured from Mitsuba Trading Co., Ltd.) and 200 mg of Polysorbate 80 (HM: product of NOF Corporation) was added 100 mg of 2,3-dihydroimidazo[2,1-b]oxazole compound (1a), giving a uniformly dispersed and suspended pharmaceutical composition.

Example 5

To a mixture solution of 200 mg of citric acid and oleic acid monoglycerol ester (Poem K-37 V: product of Riken Vitamin Co., Ltd.) and 100 mg of medium chain fatty acid triglycerides (ODO-H: product of Nisshin OilliO Group, Ltd.) was added 50 mg of caffeine (product of Wako Pure Chem. Ind. Ltd.), giving a uniformly dispersed and suspended pharmaceutical composition.

Example 6

To a mixture solution of 200 mg of fatty acid and organic acid glycerol ester (Glyceryl citrate/lactate/linoleate/oleate, Imwitor 375: procured from Mitsuba Trading Co., Ltd.) and 100 mg of a propylene glycol fatty acid ester (Miglyol 840: procured from Mitsuba Trading Co., Ltd.) was added 50 mg of caffeine (product of Wako Pure Chem. Ind. Ltd.), giving a uniformly dispersed and suspended pharmaceutical composition.

Comparative Example 1

A core composition having the following components was granulated by fluidized bed granulation, and then subjected to tablet compression in such a manner that the weight of one tablet was 278 mg. A coating film was applied to the resultant tablets in such a manner that the weight of one tablet was 286 mg, and tablet diameter was 9 mm.
<Core Composition>

| | |
|---|---|
| 2,3-dihydroimidazo[2,1-b]oxazole compound (1a) | 100 mg |
| lactose | q.s. |
| crystalline cellulose | q.s. |
| binder | q.s. |
| disintegrator | q.s. |
| lubricant | q.s. |
| Total | 278 mg |

Comparative Example 2

To a mixture solution of 320 mg of medium chain fatty acid triglyceride (ODO-H: product of Nisshin OilliO Group, Ltd.) and 80 mg of a hydrophilic surfactant (Cremophore EL: product of BASF) was added 100 mg of 2,3-dihydroimidazo[2,1-b]oxazole compound (1a), giving a uniformly dispersed and suspended pharmaceutical composition.

Comparative Example 3

To a mixture solution of 100 mg of a propylene glycol fatty acid ester (Miglyol 840: procured from Mitsuba Trading Co., Ltd.), 100 mg of succinic acid (product of Wako Pure Chemical Industries, Ltd.) and 367 mg of Polysorbate 80 (HM: product of NOF Corporation) was added 100 mg of 2,3-dihydroimidazo[2,1-b]oxazole compound (1a), giving a uniformly dispersed and suspended pharmaceutical composition.

Comparative Test Example 1

A capsule preparation prepared by placing a 286 mg coated tablet of Comparative Example 1 in a gelatin capsule for animals (product name: Japanese Pharmacopoeia-specified capsule No. 13, ⅛ oz, product of Torpac Inc.) was orally administered to each of four beagles with empty stomachs. Blood was collected time to time, and the concentration of pharmacologically active substance in the blood (concentration of 2,3-dihydroimidazo[2,1-b]oxazole compound (1a) in the blood) was measured. The same experiments were conducted using capsule preparations prepared by placing 500 mg of the suspended pharmaceutical composition of Comparative Example 2 in a gelatin capsule (product name: Japanese Pharmacopoeia-specified capsule No. 13, ⅛ oz, product of Torpac Inc.).

FIG. 1 shows the change in concentration of pharmacologically active substance in the blood, and Table 1 shows the average pharmacokinetic parameters. The results indicate that there is no significant difference between the tablet of Comparative Example 1 and suspended pharmaceutical composition of Comparative Example 2 in absorbency, and improvement in absorbency of the poorly soluble 2,3-dihydroimidazo[2,1-b]oxazole compound (1a) was not observed even when the compound was suspended in an oily composition.

TABLE 1

| | $C_{max}$ (ng/ml) | $AUC_{24\,hr}$ (hr · ng/ml) |
|---|---|---|
| Comparative Example 1 | 59 ± 27 | 455 ± 317 |
| Comparative Example 2 | 41 ± 7 | 500 ± 677 |

$AUC_{24\,hr}$: The area under the plasma concentration time curve until 24 hours from administration (hr · ng/ml)
$C_{max}$: The maximum concentration in the blood (ng/ml)

Comparative Test Example 2

A capsule preparation prepared by placing 500 mg of suspended pharmaceutical composition of Comparative Example 2 in a gelatin capsule for animals (product name: Japanese Pharmacopoeia-specified capsule No. 13, ⅛ oz, product of Torpac Inc.) was orally administered to each of two beagles with empty stomachs.

Blood was collected time to time, and the concentration of pharmacologically active substance in the blood (concentration of 2,3-dihydroimidazo[2,1-b]oxazole compound (1a) in the blood) was measured. The same experiments were conducted using capsule preparations prepared by placing 667 mg of suspended pharmaceutical composition of Comparative Example 3 in a gelatin capsule (product name: Japanese Pharmacopoeia-specified capsule No. 13, ⅛ oz, product of Torpac Inc.).

Figure 2:
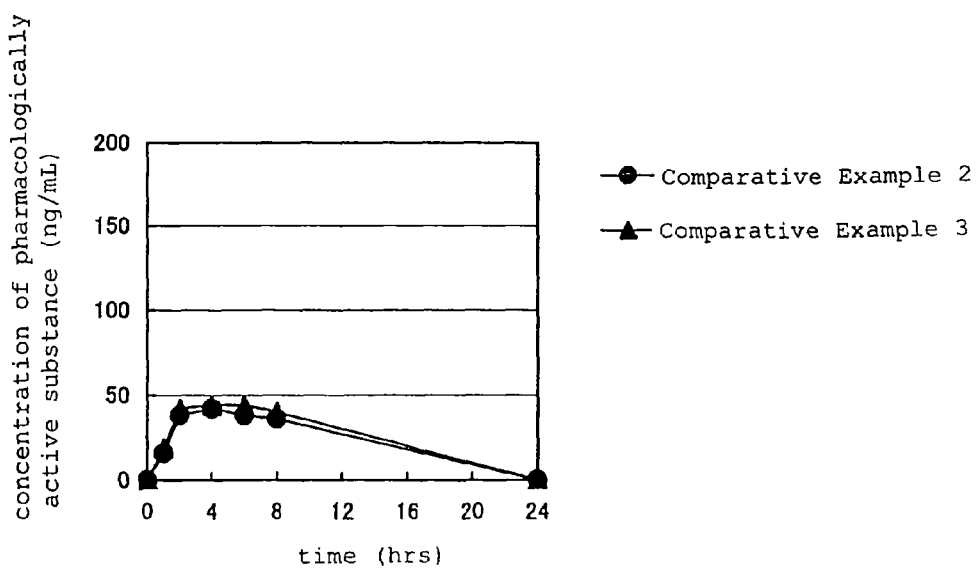
FIG. 2 shows the change over time of the average concentration of pharmacologically active substance (2,3-dihydroimidazo[2,1-b]oxazole compound (1a)) in the blood in Comparative Test Example 2, when the pharmaceutical composition of Comparative Example 2 or 3 was orally administered to beagles.

FIG. 2 shows the change in concentration of pharmacologically active substance in the blood, and Table 2 shows the average pharmacokinetic parameters. The results indicate that there is no significant difference between the suspended pharmaceutical composition of Comparative Example 2 and the suspended pharmaceutical composition of Comparative Example 3 in absorbency, and improvement in absorbency of the pharmacologically active substance was not observed by merely adding an organic acid (succinic acid).

TABLE 2

|  | $C_{max}$ (ng/ml) | $AUC_{24\,hr}$ (hr · ng/ml) |
|---|---|---|
| Comparative Example 2 | 46 ± 6 | 556 ± 30 |
| Comparative Example 3 | 54 ± 1 | 614 ± 156 |

$AUC_{24\,hr}$: The area under the plasma concentration time curve until 24 hours from administration (hr · ng/ml)
$C_{max}$: The maximum concentration in the blood (ng/ml)

Test Example 1

A capsule preparation prepared by placing 700 mg of the suspended pharmaceutical composition of Example 1 in a gelatin capsule for animals (product name: Japanese Pharmacopoeia-specified capsule No. 13, ⅛ oz, product of Torpac Inc.) was orally administered to each of three beagles with empty stomachs. Blood was collected time to time, and the concentration of pharmacologically active substance in the blood (concentration of 2,3-dihydroimidazo[2,1-b]oxazole compound (1a) in the blood) was measured. The same experiments were conducted using capsule preparations prepared by placing 700 mg of the suspended pharmaceutical composition of Example 2 in a gelatin capsule (product name: Japanese Pharmacopoeia-specified capsule No. 13, ⅛ oz, product of Torpac Inc.). The same experiments were conducted using capsule preparations prepared by placing 286 mg of coating tablet of Comparative Example 1 in a gelatin capsule (product name: Japanese Pharmacopoeia-specified capsule No. 13, ⅛ oz, product of Torpac Inc.).

Figure 3:
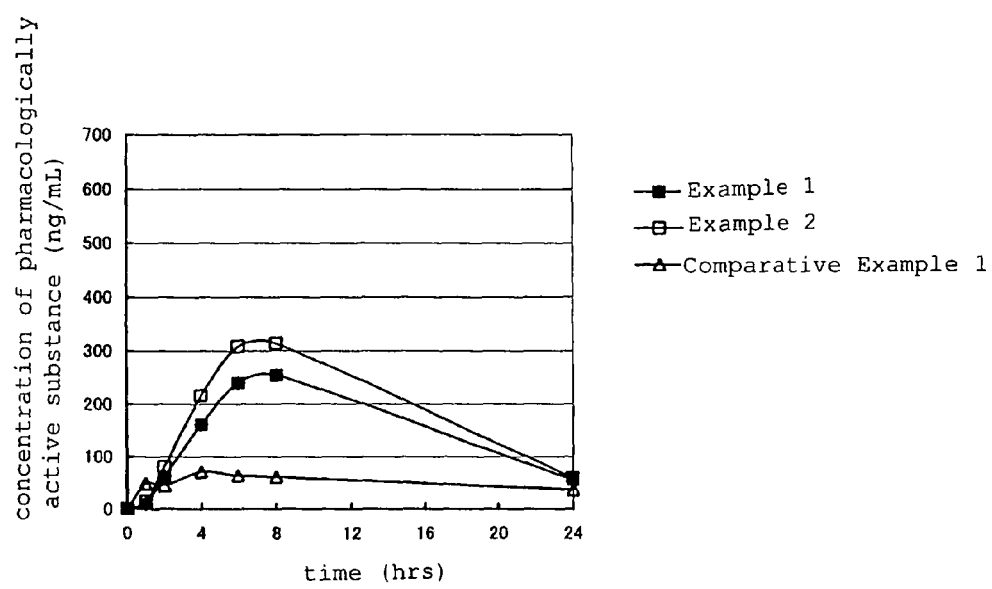
FIG. 3 shows the change over time of the average concentration of pharmacologically active substance (2,3-dihydroimidazo[2,1-b]oxazole compound (1a)) in the blood in Test Example 1, when the pharmaceutical composition of Example 1 or 2 or Comparative Example 1 was orally administered to beagles.

FIG. 3 shows the change in concentration of pharmacologically active substance in the blood, and Table 3 shows the average pharmacokinetic parameters. The results indicate that the suspended pharmaceutical compositions of Examples 1 and 2 exhibit remarkable improvement in absorbency of the pharmacologically active substance compared to the coated tablets of Comparative Example 1.

TABLE 3

|  | $C_{max}$ (ng/ml) | $AUC_{24\,hr}$ (hr · ng/ml) |
|---|---|---|
| Example 1 | 275 ± 96 | 3648 ± 1283 |
| Example 2 | 341 ± 289 | 4491 ± 4004 |
| Comparative Example 1 | 84 ± 23 | 1228 ± 348 |

$AUC_{24\,hr}$: The area under the plasma concentration time curve until 24 hours from administration (hr · ng/ml)
$C_{max}$: The maximum concentration in the blood (ng/ml)

As is clear form the results of adding a fatty acid and organic acid glycerol ester and/or a fatty acid and organic acid polyglycerol ester to a basic pharmacologically active substance, absorbency of an orally taken basic pharmacologically active substance can be improved.

The invention claimed is:

1. A pharmaceutical composition comprising:
Component (i) a basic pharmacologically active substance comprising a 2,3-dihydroimidazo[2,1-b]oxazole compound represented by General Formula (I):

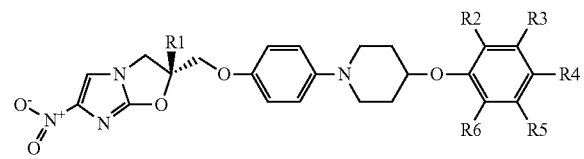

(1)

wherein R1 is a hydrogen atom or a $C_1$-$C_6$ alkyl group; and R2-R6 are independently a hydrogen atom, or a halogen substituted or unsubstituted $C_1$-$C_6$ alkyl group, and Component (ii) a compound wherein one or two fatty acids and one or two organic acids are linked to a glycerol ester linkages, and/or a compound wherein one or two fatty acids and one or two organic acids are linked to a polyglycerol by ester linkages, wherein the organic acid of component (ii) is at least one member chosen from citric acid, acetic acid, lactic acid, succinic acid, tartaric acid, diacetyltartaric acid, malic acid, ascorbic acid, and fumaric acid.

2. A pharmaceutical composition according to claim 1, wherein the basic pharmacologically active substance of Component (i) is a poorly soluble basic pharmacologically active substance.

3. A pharmaceutical composition according to claim 1, wherein the constituent organic acid of Component (ii) is a divalent or higher valent organic acid having carboxyl group(s).

4. A pharmaceutical composition according to claim 1, wherein the constituent fatty acid of Component (ii) is a saturated or unsaturated $C_6$-$C_{24}$ fatty acid.

5. A pharmaceutical composition according to claim 1, wherein Component (ii) is at least one member selected from the group consisting of citric acid and fatty acid glycerol esters, acetic acid and fatty acid glycerol esters, lactic acid and fatty acid glycerol esters, succinic acid and fatty acid glycerol esters, fumaric acid and fatty acid glycerol esters, tartaric acid and fatty acid glycerol esters, diacetyltartric acid and fatty acid glycerol esters, citric acid and fatty acid polyglycerol esters, polyacetic acid and fatty acid glycerol esters, lactic acid and fatty acid polyglycerol esters, succinic acid and fatty acid polyglycerol esters, fumaric acid and fatty acid polyglycerol esters, tartaric acid and fatty acid polyglycerol esters, and diacetyltartric acid and fatty acid polyglycerol esters.

6. A pharmaceutical composition according to claim 1, wherein Component (ii) is a compound wherein one or two fatty acids and one or two organic acids are linked to a glycerol by ester linkages, wherein the constituent organic acid is citric acid and the constituent fatty acid is at least one member selected from the group consisting of caprylic acid, stearic acid, oleic acid, and behenic acid.

7. A pharmaceutical composition according to claim 1, which contains 10 to 100,000 parts by weight of Component (ii) per 100 parts by weight of Component (i).

8. A pharmaceutical composition according to claim 1, which contains 0.1 to 80 wt. % of Component (i) and 1 to 99.5 wt. % of Component (ii) of total weight of pharmaceutical composition.

9. A pharmaceutical composition according to claim 1, which further contains at least one member selected from the group consisting of oil-based materials, hydrophilic surfactants, and oleophilic surfactants.

10. A method for preparing a basic pharmacologically active substance-containing pharmaceutical composition comprising the step of combining:
(i) a basic pharmacologically active substance comprising a 2,3-dihydroimidazo[2,1-b]oxazole compound represented by General Formula (I):

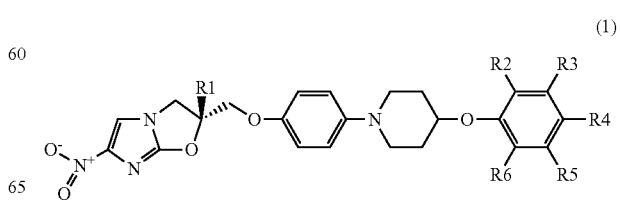

(1)

wherein R1 is a hydrogen atom or a $C_1$-$C_6$ alkyl group; and R2-R6 are independently a hydrogen atom, or a halogen substituted or unsubstituted $C_1$-$C_6$ alkyl group; with (ii) a compound wherein one or two fatty acids and one or two organic acids are linked to a glycerol by ester linkages, and/or a compound wherein one or two fatty acids and one or two organic acids are linked to a polyglycerol by ester linkages, wherein the organic acid is at least one member chosen from citric acid, acetic acid, tactic acid, succinic acid, tartaric acid, diacetyltartaric acid, malic acid, ascorbic acid, and fumaric acid.

* * * * *